United States Patent [19]

Moon et al.

[11] 4,115,649

[45] Sep. 19, 1978

[54] PHENYL PYRAZOLE MORPHOLINE AMIDES

[75] Inventors: Malcolm W. Moon; Gabriel Kornis, both of Kalamazoo, Mich.

[73] Assignee: The Upjohn Company, Kalamazoo, Mich.

[21] Appl. No.: 846,181

[22] Filed: Oct. 27, 1977

Related U.S. Application Data

[60] Division of Ser. No. 686,548, May 14, 1976, Pat. No. 4,072,498, which is a continuation-in-part of Ser. No. 524,231, Nov. 15, 1974, abandoned.

[51] Int. Cl.² ........................................... C07D 413/06
[52] U.S. Cl. .................................................. 544/140
[58] Field of Search ......................................... 544/140

[56] References Cited

U.S. PATENT DOCUMENTS 3,957,480   5/1976   Kornis ................................. 544/140

*Primary Examiner*—Henry R. Jiles
*Assistant Examiner*—R. W. Ramsuer
*Attorney, Agent, or Firm*—Bruce Stein; John J. Killinger

[57] ABSTRACT

The present invention discloses amides and thioamides substituted in the α or β position with substituted pyrazoles which are useful as herbicides.

2 Claims, No Drawings

PHENYL PYRAZOLE MORPHOLINE AMIDES

CROSS REFERENCE TO RELATED APPLICATION

This is a division of application Ser. No. 686,548, filed May 14, 1976, now U.S. Pat No. 4,072,498 which in turn is a continuation in part of application Ser. No. 524,231, filed Nov. 15, 1974, now abandoned.

The present invention relates to phenyl pyrazole morpholine amides, for which the essential material constituting a disclosure thereof is incorporated by reference here from U.S. patent application Ser. No. 686,548, filed May 14, 1976, now U.S. Pat. No. 4,072,498.

We claim:

1. A compound of the formula:

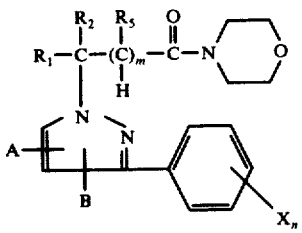

where $R_1$ is hydrogen, alkyl of 1 to 7 carbon atoms, inclusive, haloalkyl of 1 to 7 carbon atoms, inclusive, phenyl, benzyl or cycloalkyl of 3 to 6 carbon atoms, inclusive, with the proviso that when $R_1$ is benzyl or cycloalkyl $m = 0$; $R_2$ and $R_5$ are the same or different and are hydrogen, halogen, alkyl of 1 to 6 carbon atoms, inclusive, haloalkyl of 1 to 6 carbon atoms, inclusive, or phenyl; $R_1$ and $R_2$ together with the attached carbon atom can be cycloalkyl of 3 to 6 carbon atoms, inclusive, when $m = 0$; $m$ is 0 or 1 provided that when $m = 0$, $R_1$ is not hydrogen and when $m = 1$ at least one of $R_2$ or $R_5$ is hydrogen; A and B are the same or different and are hydrogen, alkyl of from 1 to 6 carbon atoms, inclusive, phenyl, halogen, cyano, haloalkyl of 1 to 6 carbon atoms, inclusive, alkoxy or alkylthio in which the alkyl group is from 1 to 3 carbon atoms, inclusive, or trifluoromethyl and when adjacent can be joined to form a ring of from 5 to 7 carbon atoms, inclusive; where X is halogen, nitro, cyano, acetyl, dimethylcarbamoyl, alkyl, haloalkyl, alkoxy or carboalkoxy in which the alkyl group is from 1 to 3 carbon atoms, inclusive, phenyl, benzyl, 2-phenylethyl and $n$ is 0, 1, or 2 or an acid addition salt thereof.

2. A compound according to claim 1 which is 4-[2-(4-methyl-3-phenylpyrazol-1-yl)propionyl]morpholine.

* * * * *